(12) United States Patent
Bright et al.

(10) Patent No.: US 12,318,106 B2
(45) Date of Patent: Jun. 3, 2025

(54) METHOD FOR USING A SURGICAL DEVICE TO TRANSECT A TRANSVERSE CARPAL LIGAMENT

(71) Applicant: Nanice Medical Solutions LLC, Ventnor, NJ (US)

(72) Inventors: Paul J. Bright, Ventnor, NJ (US); John L. Washeleski, Ventnor, NJ (US); Jon Hernandez, Ventnor, NJ (US)

(73) Assignee: Nanice Medical Solutions, LLC, Ambler, PA (US)

( * ) Notice: Subject to any disclaimer, the term of this patent is extended or adjusted under 35 U.S.C. 154(b) by 340 days.

(21) Appl. No.: 17/823,549

(22) Filed: Aug. 31, 2022

(65) Prior Publication Data

US 2023/0076813 A1     Mar. 9, 2023

Related U.S. Application Data

(63) Continuation-in-part of application No. 17/067,710, filed on Oct. 11, 2020, which is a continuation-in-part of application No. 16/001,887, filed on Jun. 6, 2018, now Pat. No. 10,806,481, which is a continuation-in-part of application No. 15/282,839, filed on Sep. 30, 2016, now Pat. No. 11,033,291.

(60) Provisional application No. 63/238,930, filed on Aug. 31, 2021, provisional application No. 62/236,728, filed on Oct. 2, 2015.

(51) Int. Cl.
*A61B 17/32* (2006.01)
*A61B 17/3211* (2006.01)

(52) U.S. Cl.
CPC .. *A61B 17/320036* (2013.01); *A61B 17/3211* (2013.01); *A61B 2017/320052* (2013.01)

(58) Field of Classification Search
CPC ........ A61B 17/320036; A61B 17/3211; A61B 2017/320052
See application file for complete search history.

(56) References Cited

U.S. PATENT DOCUMENTS 5,323,765 A * 6/1994 Brown ........... A61B 17/320036
600/109
5,507,800 A   4/1996 Strickland
(Continued)

FOREIGN PATENT DOCUMENTS

WO    2015171785 A1    11/2015

OTHER PUBLICATIONS

Non-Final Office Action received for U.S. Appl. No. 16/001,887, mailed on Aug. 22, 2019, 13 pages.
(Continued)

*Primary Examiner* — Sarah A Long
*Assistant Examiner* — Raihan R Khandker
(74) *Attorney, Agent, or Firm* — Schott, P.C.

(57) ABSTRACT

A disposable, sterile guide constructed of medically-acceptable plastic used for compartmentalizing and therefore protecting the ligament or fascia during three different orthopedic surgical procedures: ECTR, ECuTR, and EPFR. This device reduces the risk of damage to any other part of the surrounding anatomy. The device is disposable and packaged so as to be sterile and therefore readily usable by the surgeon means that it can reduce the risk of infection and is a less expensive alternative to traditional non-disposable, metal instruments that must be sterilized prior to each procedure.

20 Claims, 17 Drawing Sheets

(56) References Cited

U.S. PATENT DOCUMENTS

| | | |
|---|---|---|
| 5,827,311 A | 10/1998 | Berelsman et al. |
| 5,908,431 A | 6/1999 | Battenfield |
| 6,283,948 B1 | 9/2001 | McKeman et al. |
| 8,252,011 B1 | 8/2012 | Forrester |
| 8,523,892 B2 | 9/2013 | Rehnke et al. |
| 8,672,960 B2 | 3/2014 | Briganti et al. |
| 8,882,772 B2 | 11/2014 | Solsberg et al. |
| 8,951,273 B1 | 2/2015 | Fard |
| 10,806,481 B2 | 10/2020 | Bright et al. |
| 11,033,291 B2 | 6/2021 | Bright et al. |
| 2005/0159730 A1 | 7/2005 | Kathrani et al. |
| 2006/0079925 A1* | 4/2006 | Kerr ............... A61B 17/0206 606/198 |
| 2008/0200758 A1 | 8/2008 | Orbay et al. |
| 2010/0063452 A1* | 3/2010 | Edelman ............ A61B 17/3421 604/174 |
| 2010/0280368 A1 | 11/2010 | Can et al. |
| 2011/0046652 A1* | 2/2011 | Rehnke ........... A61B 17/320036 606/170 |
| 2014/0066709 A1 | 3/2014 | Mirza et al. |
| 2014/0121456 A1 | 5/2014 | McCormack et al. |
| 2014/0371526 A1 | 12/2014 | Mirza et al. |
| 2015/0272617 A1 | 10/2015 | MacDonald |
| 2016/0157881 A1 | 6/2016 | Seymour et al. |
| 2016/0192828 A1 | 7/2016 | Sexton |
| 2016/0287322 A1 | 10/2016 | Solsberg |
| 2016/0345998 A1* | 12/2016 | Seymour ........ A61B 17/320036 |
| 2021/0106352 A1 | 4/2021 | Bright et al. |

OTHER PUBLICATIONS

Final Office Action received for U.S. Appl. No. 16/001,887, mailed on Jan. 8, 2020, 19 pages.
Notice of Allowance received for U.S. Appl. No. 16/001,887, mailed on Jun. 18, 2020, 9 pages.
Einhorn, N. and Leddy, J.P., "Pitfalls of Endosopic Carpal Tunnel Release,"Oorthopedic Clinic of North America, vol. 27, No. 2, pp. 373-380 (1996).
Microaire Sugical Instruments, "SmartRelease ECTR Endoscopic Carpal Tunnel Release Surgical Technique", Entire Document, Charlottesville, VA., United States, pp. 1-16 (2011).
Smith&Nephew, "Ectra II Carpal Ligament system", US Professional, United States, pp. 1-3 (2016).
Final Office Action received for U.S. Appl. No. 15/282,839, mailed on Aug. 4, 2020, 9 pages.
Final Office Action received for U.S. Appl. No. 15/282,839, mailed on Jun. 25, 2019, 10 pages.
Non Final Office Action received for U.S. Appl. No. 15/282,839, mailed on Jan. 27, 2020, 10 pages.
Non Final Office Action received for U.S. Appl. No. 15/282,839, mailed on Jan. 11, 2019, 10 pages.
Arthrex Inc., "Centerline Endoscopic Carple Tunnel Release," Surgical Technique, Brochure No. LT1-0412-EN_C, pp. 1-6 (2015).

* cited by examiner

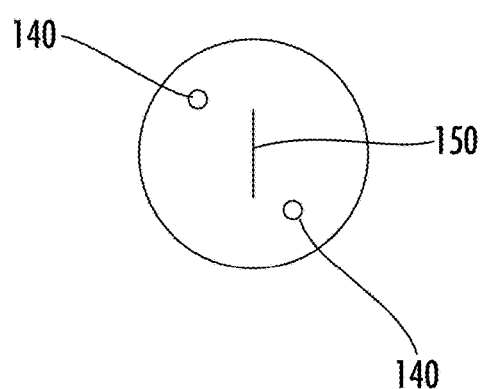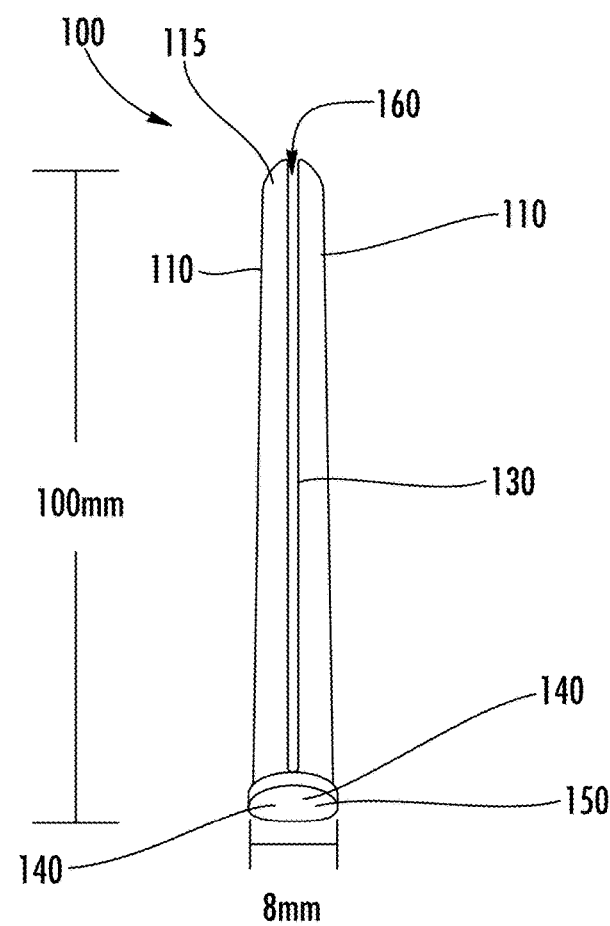
FIG. 2A
FIG. 2B

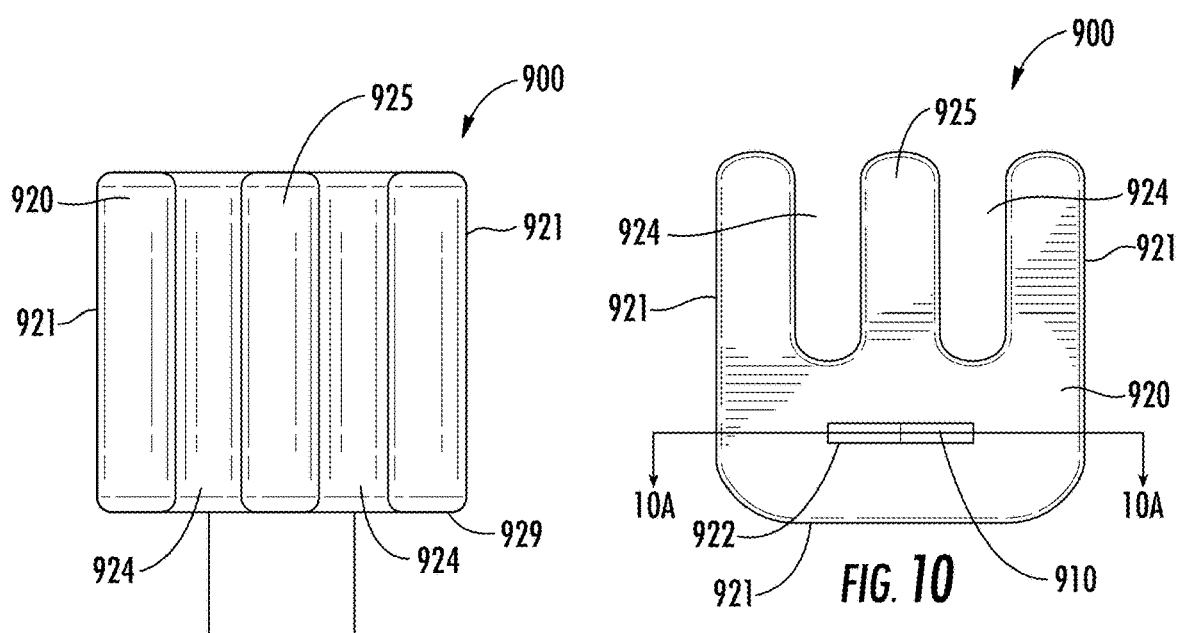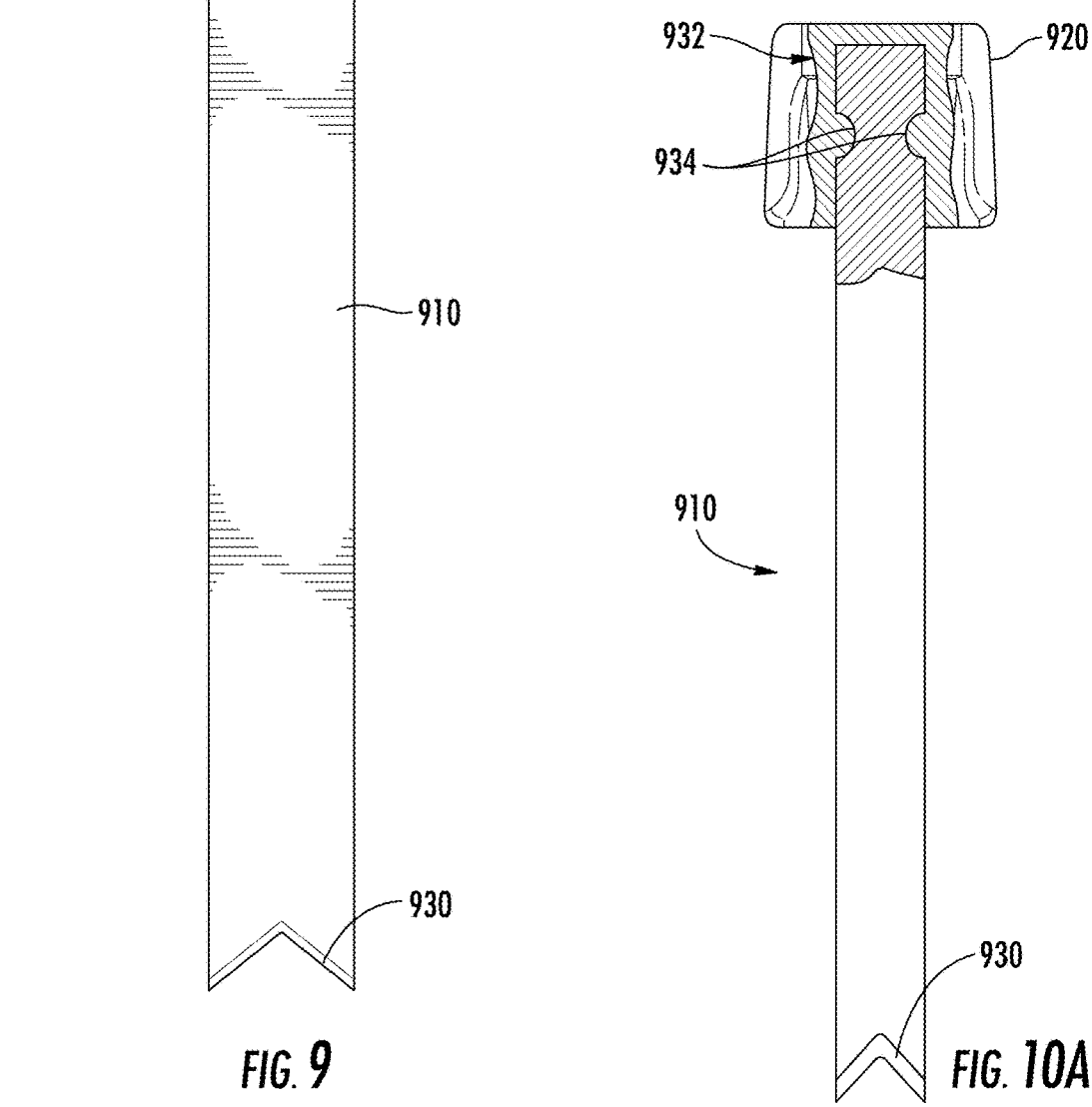
FIG. 9
FIG. 10
FIG. 10A

METHOD FOR USING A SURGICAL DEVICE TO TRANSECT A TRANSVERSE CARPAL LIGAMENT

BACKGROUND

Endoscopic Carpal Tunnel Release (ECTR), Endoscopic Cubital Tunnel Release (ECuTR), and Endoscopic Plantar Fasciitis Release (EPFR) are three surgical procedures used to relieve symptoms in the hand, elbow, and heel, respectively. During each procedure, the surgeon makes a small incision and inserts a thin tube called an endoscope with a tiny camera attached to it to view the affected area. The surgeon then inserts a cutting instrument through this same, single portal to perform the procedure. The benefit of endoscopic procedures is that they require smaller incisions, leading to the diminution of early post-operative pain, decreasing the amount of recovery time, and expediting patients' return to regular activity. These smaller incisions, however, inherently mean that visualization of the affected area is more restricted as compared to procedures such as Open Carpal Tunnel Release (OCTR), during which one large incision is employed. Throughout the history of endoscopic procedures, surgeons have worked to improve methods of visualization in order to improve safety levels and outcomes.

Current guides for surgery are usually stainless steel and come in two pieces, which means there are sterility issues between surgeries and also the ever-present risk of the pieces becoming unattached in surgical contexts. This is especially true because current scope pieces engage one another in a friction attachment.

SUMMARY OF THE EMBODIMENTS

The device described herein is a disposable, sterile guide constructed of medically-acceptable plastic used for compartmentalizing and therefore protecting the ligament or fascia during three different orthopedic surgical procedures: ECTR, ECuTR, and EPFR. This device reduces the risk of damage to any other part of the surrounding anatomy. The fact that the device is disposable and packaged so as to be sterile and therefore readily usable by the surgeon means that it can reduce the risk of infection and is a less expensive alternative to traditional non-disposable, metal instruments that must be sterilized before each procedure.

BRIEF DESCRIPTION OF THE DRAWINGS

FIGS. 2A and 2B show side and elevation views of the device.

FIGS. 9 and 10 show side and top views of a blade.

FIG. 10A is a cross section through 10A-10A shown in FIG. 10.

FIGS. 10, 11, 12A, 12B, and 13 show combinations of the blade and device, as well as a camera, in use.

DETAILED DESCRIPTION OF THE EMBODIMENTS

Figure 1:
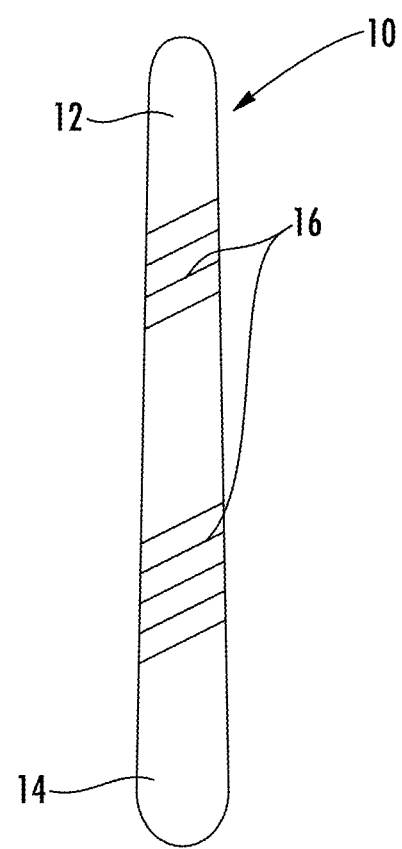
FIG. 1 shows a dilator used to prepare a surgical area for the device.

The following surgical description may be employed for using the surgical device shown in the figures in at least three different surgeries: Endoscopic Carpal Tunnel Release (Hand), Endoscopic Cubital Tunnel Release (Elbow), and Endoscopic Plantar Fasciitis Release (Heel).

After making an incision, the surgeon may use a dilator 10 (FIG. 1) to dilate the surgical area. The dilator may be about 6 inches long and taper at a broader end 14 to a narrow end 12 from 6 mm to 4 mm. The dilator may include hand grips 16 marked to minimize slipping.

To make room for the guide device to fit atop and below the targeted ligament or fascia, the surgeon may insert the device 100, 300, 400 in order to compartmentalize the ligament or fascia. The surgeon may then use the endoscope that has been inserted through a cameral passage or hole to visualize the ligament or fascia area to ensure that there are no other parts of the anatomy, such as nerves or tendons, obstructing the incision path.

If the incision path is clear, the surgeon can either antegrade cut or retrograde cut the ligament or fascia in a safe environment by inserting the knife through the appropriate slot, because the device or guide has helped the surgeon to compartmentalize the ligament or fascia to be incised, isolating it from other parts of the anatomy that could otherwise be in jeopardy of being inadvertently cut.

The endoscopic camera and the knife may work independently of each other inside the guide, making it safer for the surgeon to look ahead of the knife when needed.

FIG. 1 is a drawing of the surgical device 100 for assistance in endoscopic surgical procedures, especially those discussed above but not necessarily limited thereto.

The surgical device 100 may be 100 mm in length, 8 mm wide, and constructed from ABS plastic. The device 100 may be hollow and cylindrical with 3 mm-thick plastic prongs 110 separated by a 2 mm gap 130. FIG. 2 shows one end of the device 100, which is closed with the exception of three holes: the upper and lower circular holes 140 may be each 2.5 mm in diameter, may be used for the endoscopic camera, and may be located on either side of the 5 mm long slot 150 used for the knife. The location of the upper and lower circular holes 140 on either side of the slot 150 gives the surgeon the ability to use the endoscopic camera to visualize the surgical field more comprehensively from many angles before a cut is made to avoid damaging other portions of the anatomy.

Figure 6A:
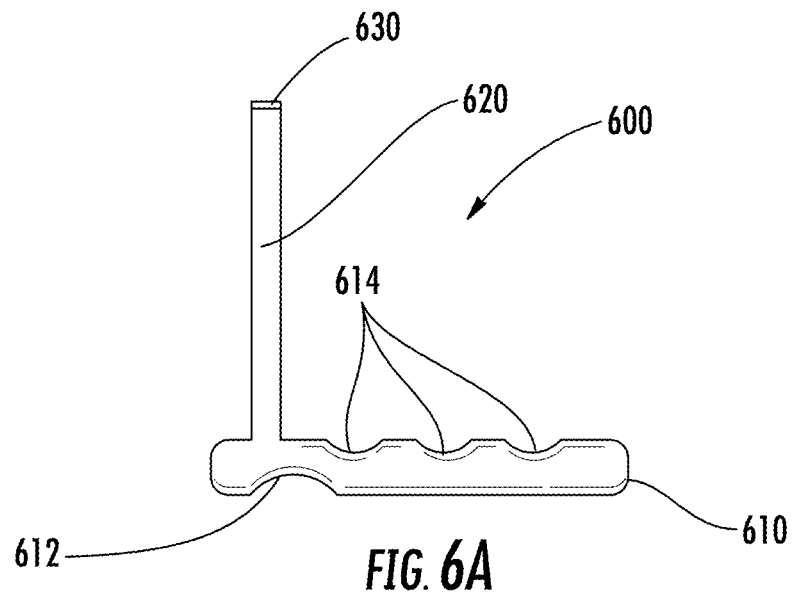
FIGS. 6A and 6B show blade and tool variants used with the device.
Figure 6B:
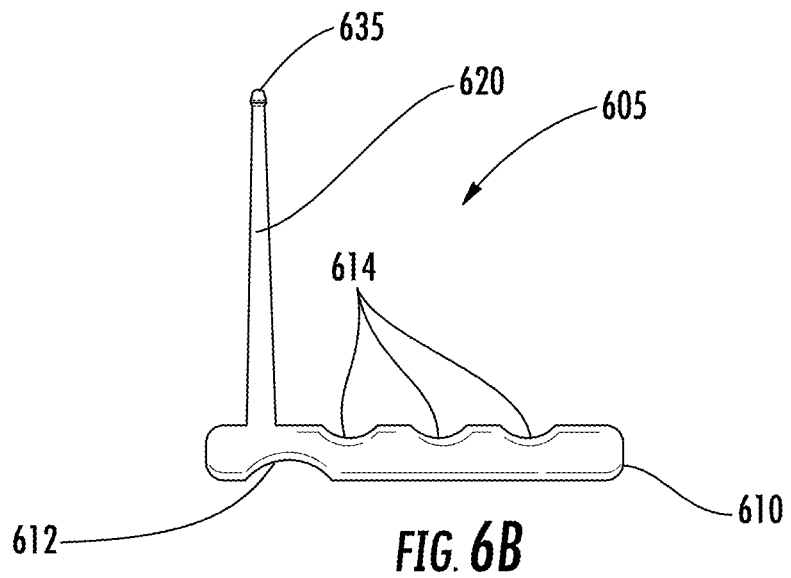

FIGS. 6A and 6B show tools like the knife (600) and wire 605 for use with the device 100, 300, or 400. In use, a surgeon may grasp the knife 600 or wire 605 by a handle 610 that may include finger cutouts for a thumb 612 and fingers 614. The tool 600, 605 may comprise both a handle portion 610 and working portion 620. On the knife 600, the working portion 620 is sized to fit within the slot 150, 380 and includes a blade 630 for performing the incisions as the blade moves within the slot 150, 380.

The wire tool 605 operates similarly to the knife tool 600 except that its working end 620 includes a narrow wire end 635 for removing fine tissue or moving a nerve out of the way of a later incision by the knife tool 600. The wire end 635 may extend in any direction (upwards towards the viewer as shown in FIG. 6B being on alternative) but importantly fits within the knife slot.

The guide device 100 may include a wedge-shaped protrusion 160 at a terminal end of one (or both) of the prongs 110 that may help in clearing tissue from within the gap 130. The wedge may be sharp, extend only from the narrow terminal end 115 of the prongs 110 or extend across the width of the prong 110.

Figure 3A:
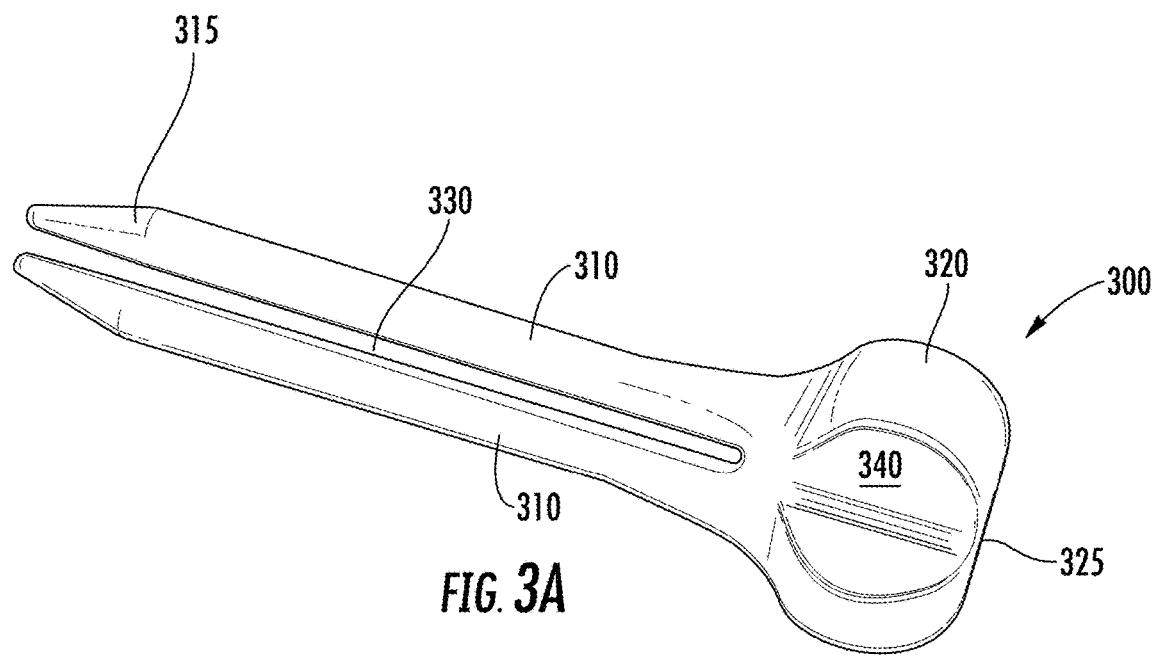
FIGS. 3A-3D show an alternate embodiment of the device.
Figure 3B:
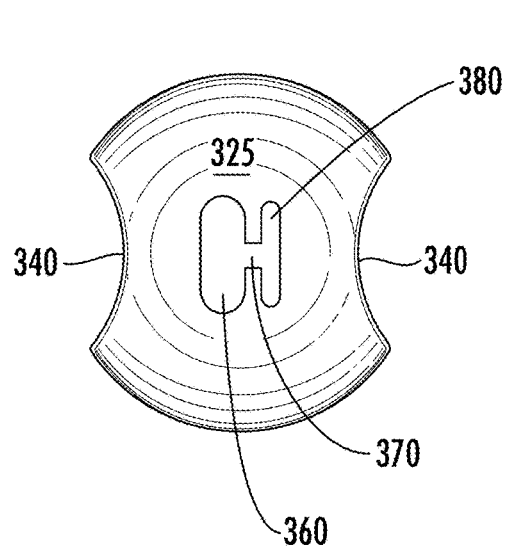
Figure 3C:
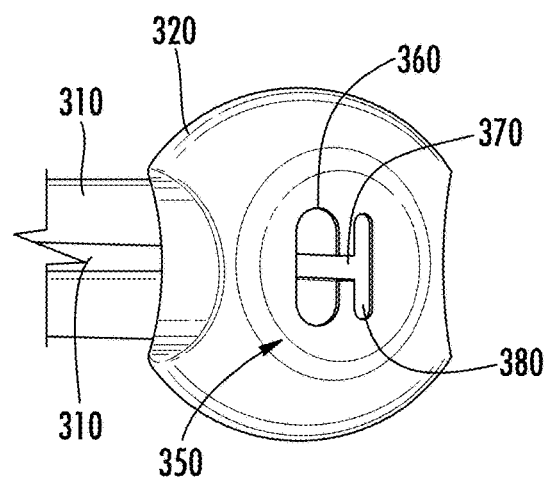
Figure 3D:
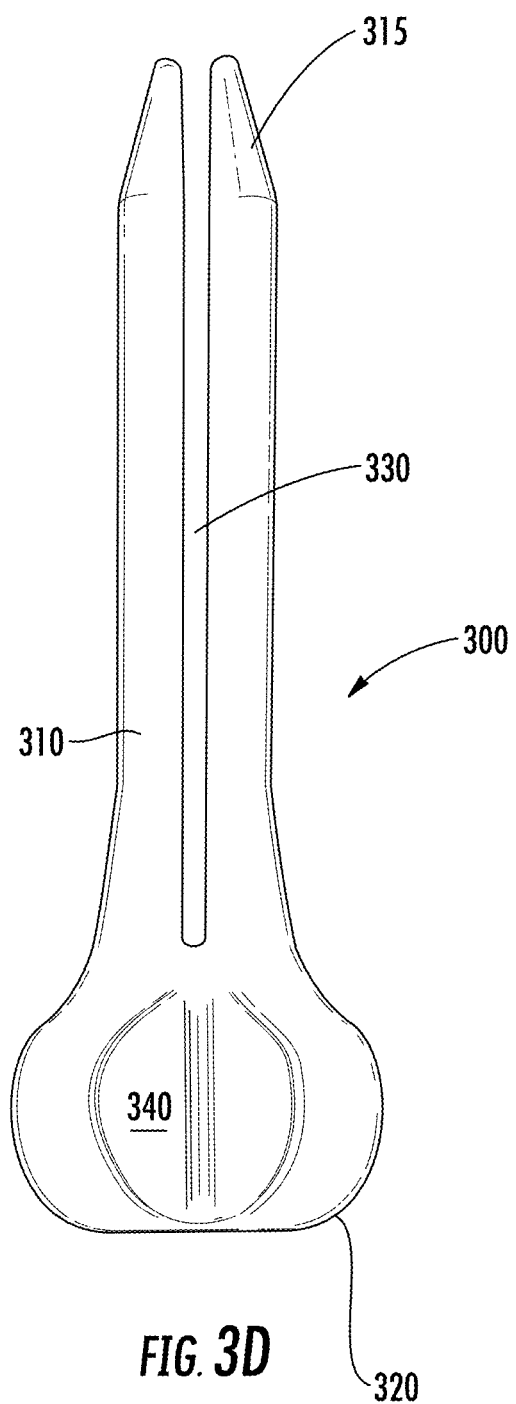

FIGS. 3A-3D show an alternate embodiment of the device from FIG. 2. As can be seen in FIG. 3A, the device 300 includes prongs 310 separated by a gap 330 similar to the geometry of FIGS. 1 and 2. The device 300's prongs 310 have a narrow terminal end 315 opposite a head portion 320 having finger cutouts 340 that in combination help in grasping the device 300. This head portion 320 helps in device 300 insertion into the patient as well as removal, and also positioning the device 300 during surgery.

The head portion end face 325 has a tool opening 350 therein. The tool opening 350 passes through the head portion 320 and is in fluid communication with the gap 330. The tool opening may include a camera opening 360 and a blade slot 380 separated by an open space 370 that allows for a small tool insertion to remove unwanted tissue or other waste from the scope or camera opening.

The camera opening is for scope insertion, and allows the surgeon to inspect the incision, ensure the area to be incised is clear of nerves, and generally allow the surgeon to see the work to be performed. As can be best seen in FIG. 4B, the camera may travel within one of the prongs 310 within a camera groove 312 formed along and within each prong 310. A second groove 314 may also include room for the tools 600, 605.

Figure 4A:
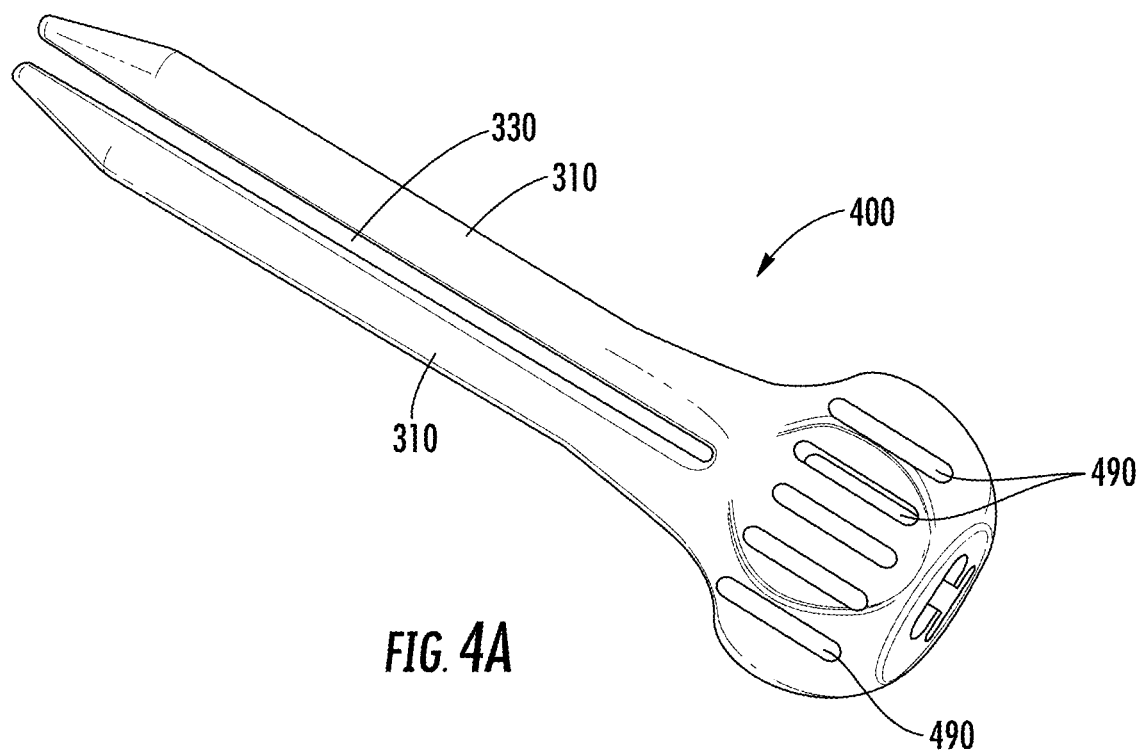
FIGS. 4A-4C show a further alternate embodiment of the device.
Figure 4B:
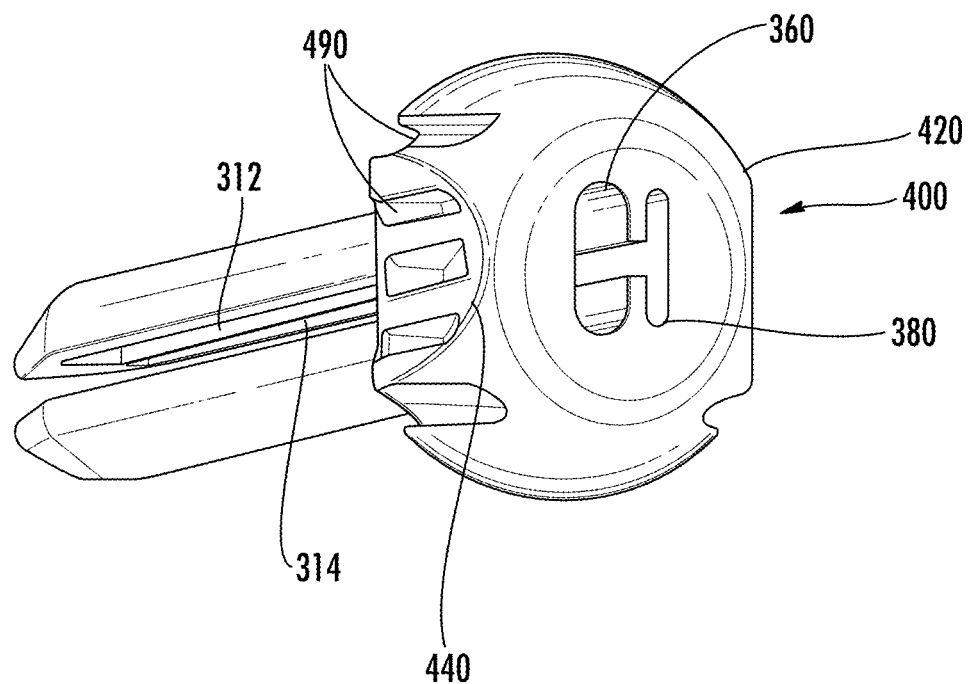
Figure 4C:
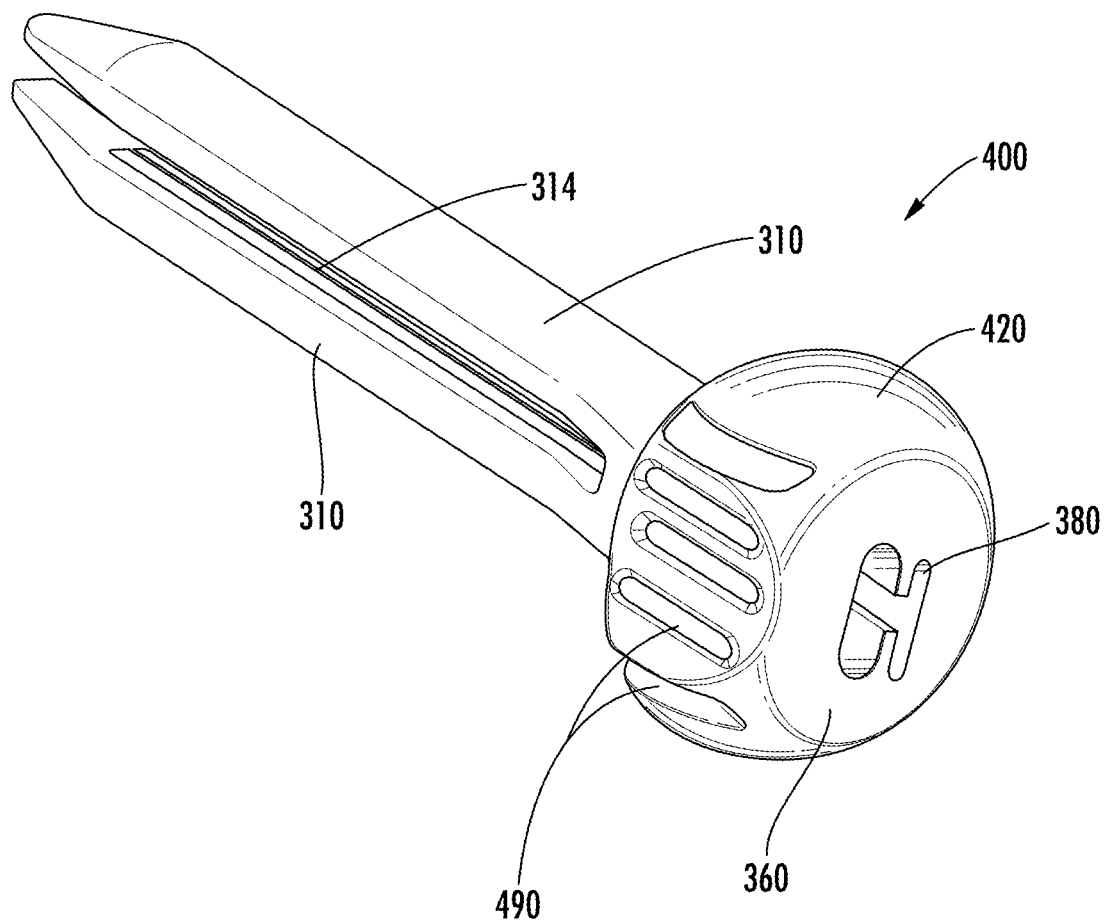

The guide device 400 in FIGS. 4A-C is similar to the one in FIGS. 3A-3D except for finger grooves 490. These finger grooves 490 extend into the head portion 420 and serve two purposes: First, they act to help a surgeon grasp the guide 400 during insertion, when slipping tools can be a problem. Second the finger grooves 490 help with cooling the device 400 during manufacture, allowing for uniform cooling and thus, decrease defect formation.

Figure 5:
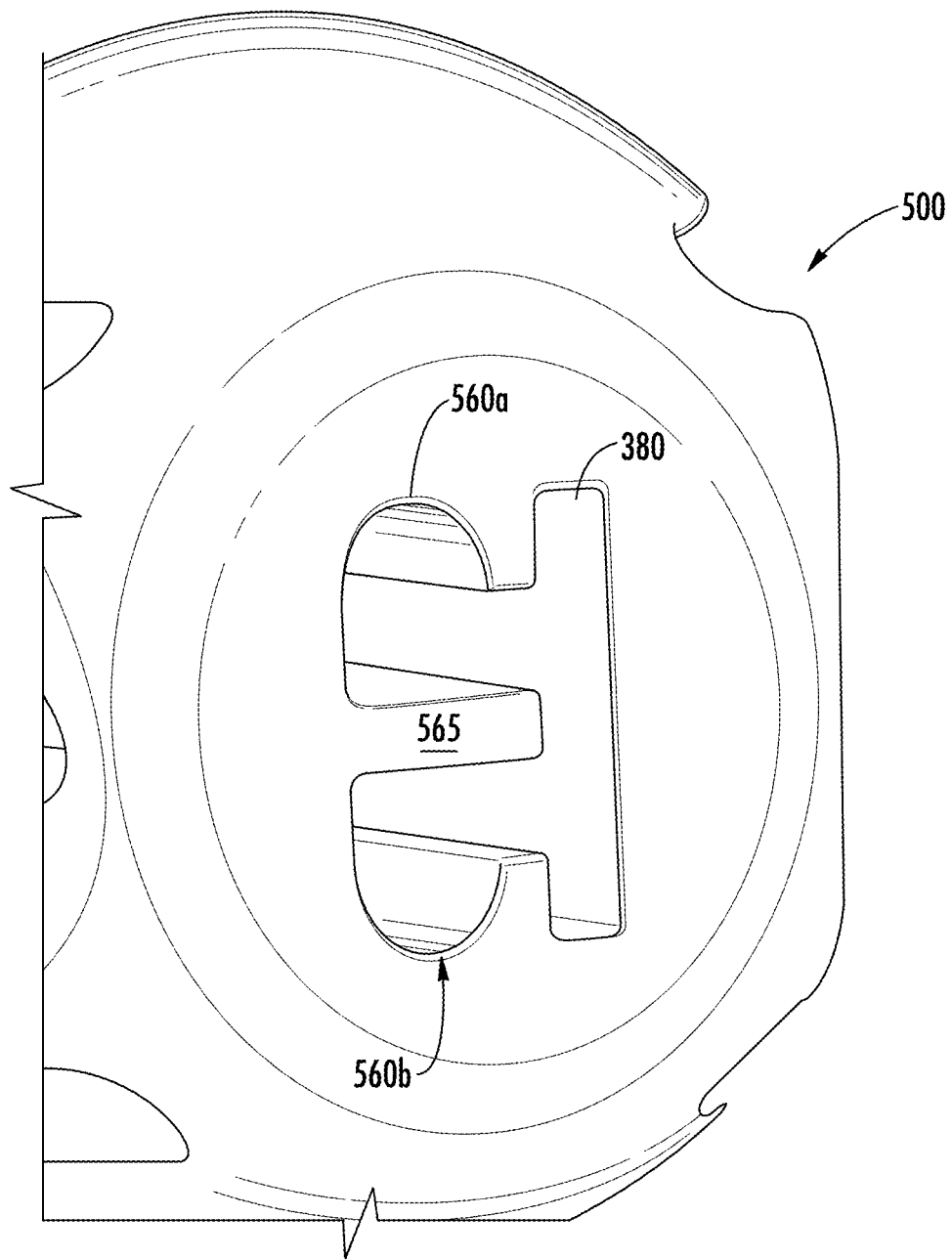
FIG. 5 shows another alternate embodiment of the device.

FIG. 5 shows a further alternate design of the device 500. Within this device, a shelf 565 extends to divide the camera opening halves 560a, and 560b. This helps support the scope when inserted into the camera openings.

Figure 7:
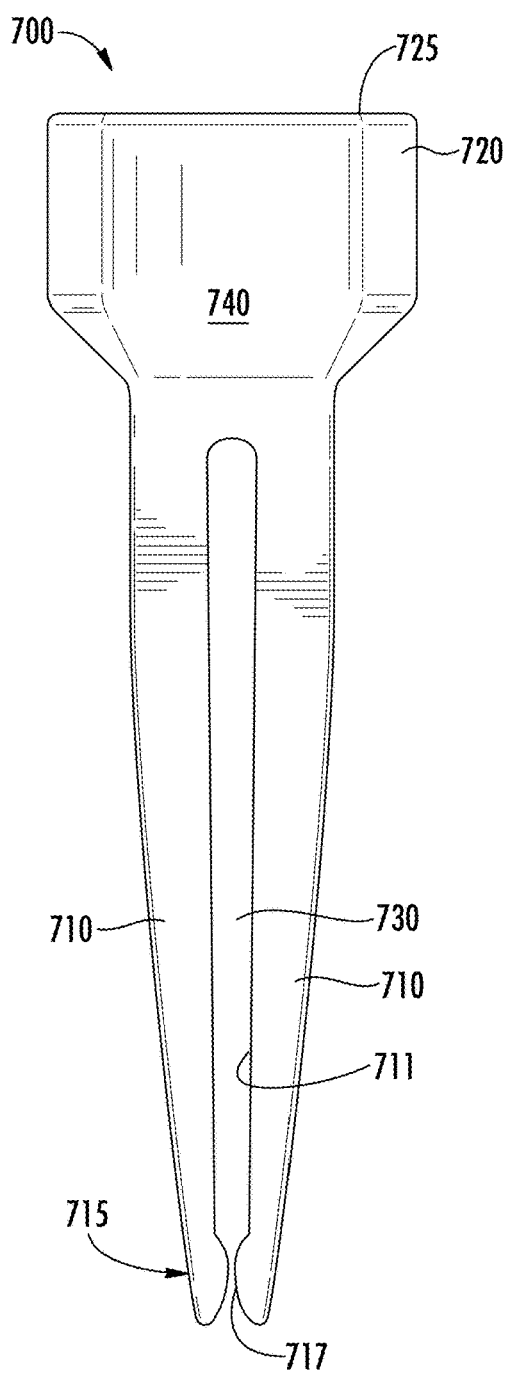
FIGS. 7 and 8 show side and top views of a further alternate embodiment of a guide device.
Figure 8:
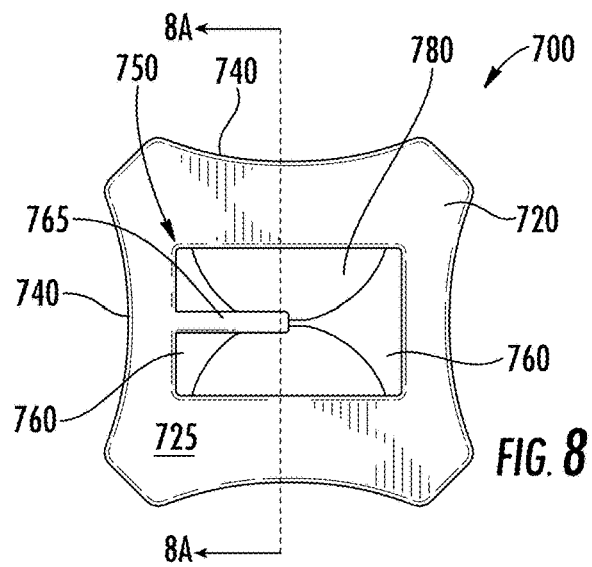

FIGS. 7 and 8 show an alternate embodiment of the guide device 700. The device has two prongs 710 that extend from a head portion 720. At a terminal end 715 of each prong 710, an engaging tooth 717 protrudes into the gap 730. The teeth 717 in practice may better engage tissue and prevent movement of the guide 700 during surgery. The teeth 717 also may prevent unwanted ingress of surrounding tissue into the gap 730, which improves visibility in the gap and also may prevent unnecessary tissue damage. The teeth 717 are preferably shaped with rounded edges to prevent catching on tissue.

The guide head portion 720 may include finger cutouts or portions 740 to assist a user in manipulating the guide 700, and these finger portions may extend from four sides of the guide to allow for easy manipulation.

It should be appreciated that similar to the guide 400 in FIG. 4C, the guide 700 of FIGS. 7-13 may include channels 712 within its prongs 710 for receiving the blade cutting tool 900 and/or camera 1210.

Figure 8A:
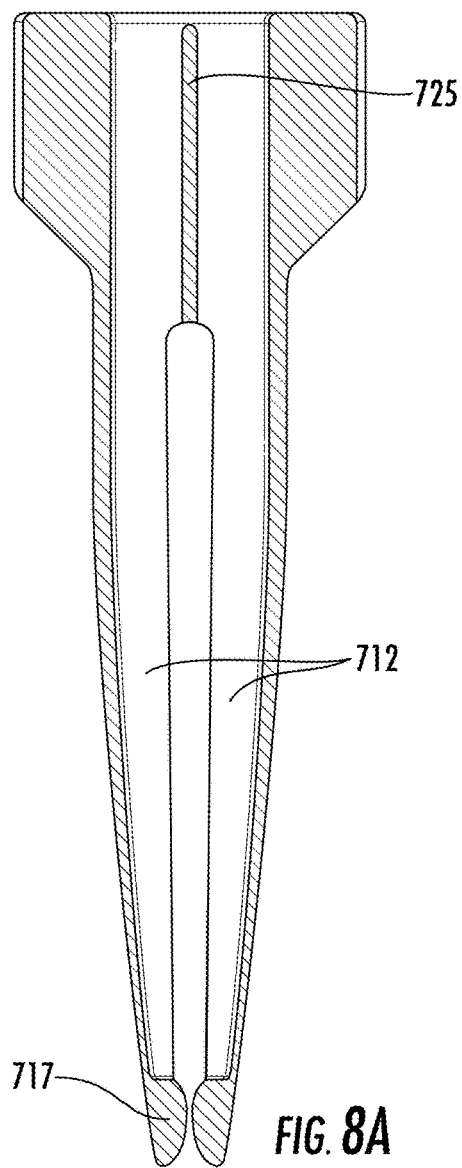
FIG. 8A is a cross section through 8A-8A shown in FIG. 8.

As best seen in FIGS. 8 and 8A, a tool opening 750 extends from the head portion 720 end face 725 and joins one or the other of the channels 712. The tool opening 750 has a blade slot 780 and a camera opening 760. The camera opening may be split by a guide portion 765 that acts as a stabilizer for the camera 1210 (see FIGS. 12A, 12B, and 13) extending into the gap 730.

FIGS. 9, 10, and 10A show an embodiment of the blade cutting tool 900 that includes a blade portion 910 and handle 920. The blade potion 910 has a cutting blade 930 for cutting tissue. The V-shape cutting blade 930 may be used, or a straight blade is possible. The material for the cutting blade may be any durable material not subject to fracture or chipping, with stainless steel being a preferred material due to its durability.

The handle 920, which may be some hardened plastic or formable material that may be sterile, may be grasped around its exterior perimeter 921, which may include finger cutout portions (not shown) to promote easier grasping. The handle 920 may include a blade receiving slot 922 that receives the blade 910 securely in the handle 920. The blade 910 may be secured to the handle 920 shortly after forming the handle such that it hardens around the blade 910, or the blade 910 may be press fit into the handle 920. As shown in FIG. 10A, the blade portion 910 includes a handle engagement end 932 that engages the handle 920, and in particular in a molded configuration where the handle 920 engages the handle engagement end 932 during the molding process, contains blade cutouts 934 to better-secure the blade portion 910 to the handle portion 920.

Figure 12A:
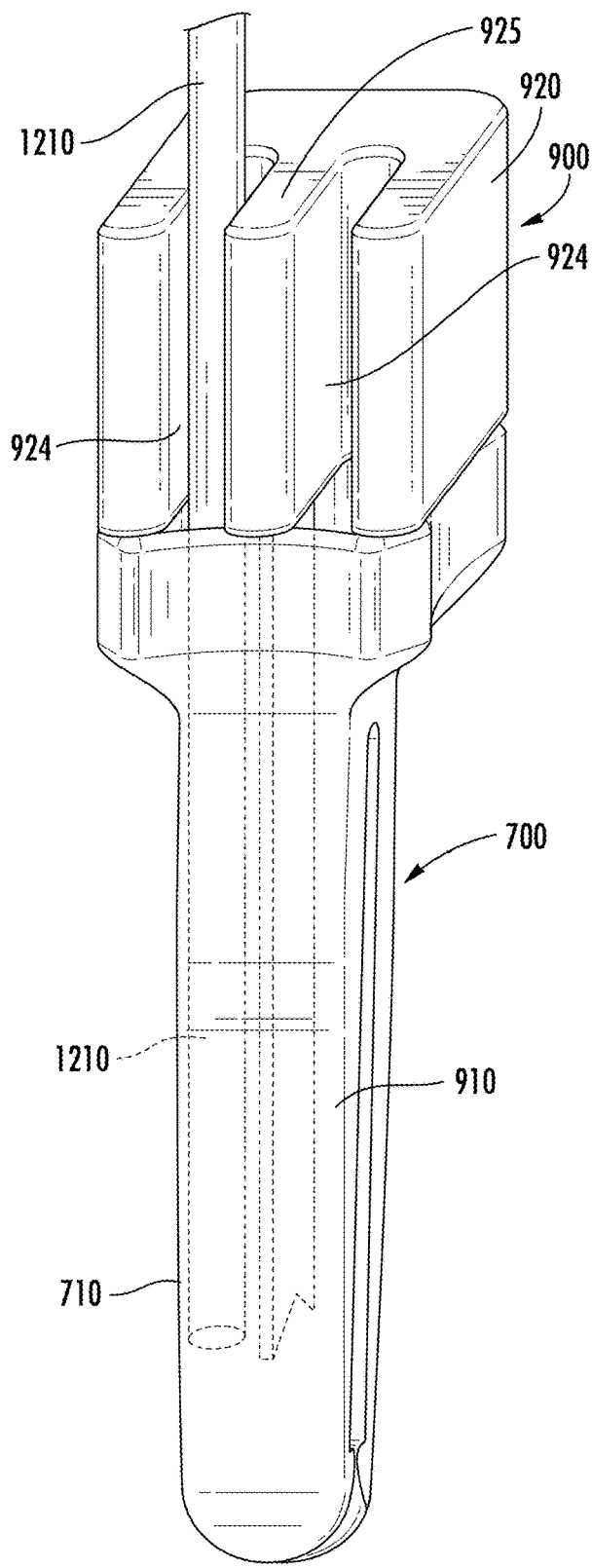
Figure 12B:
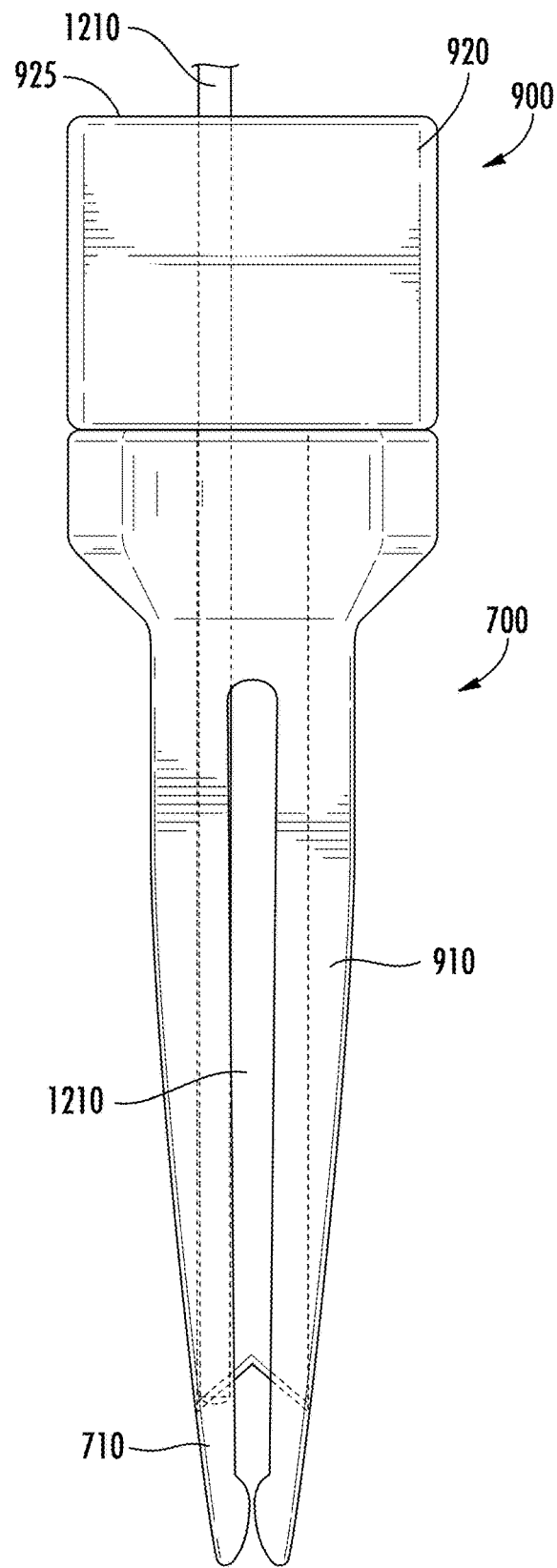
Figure 13:
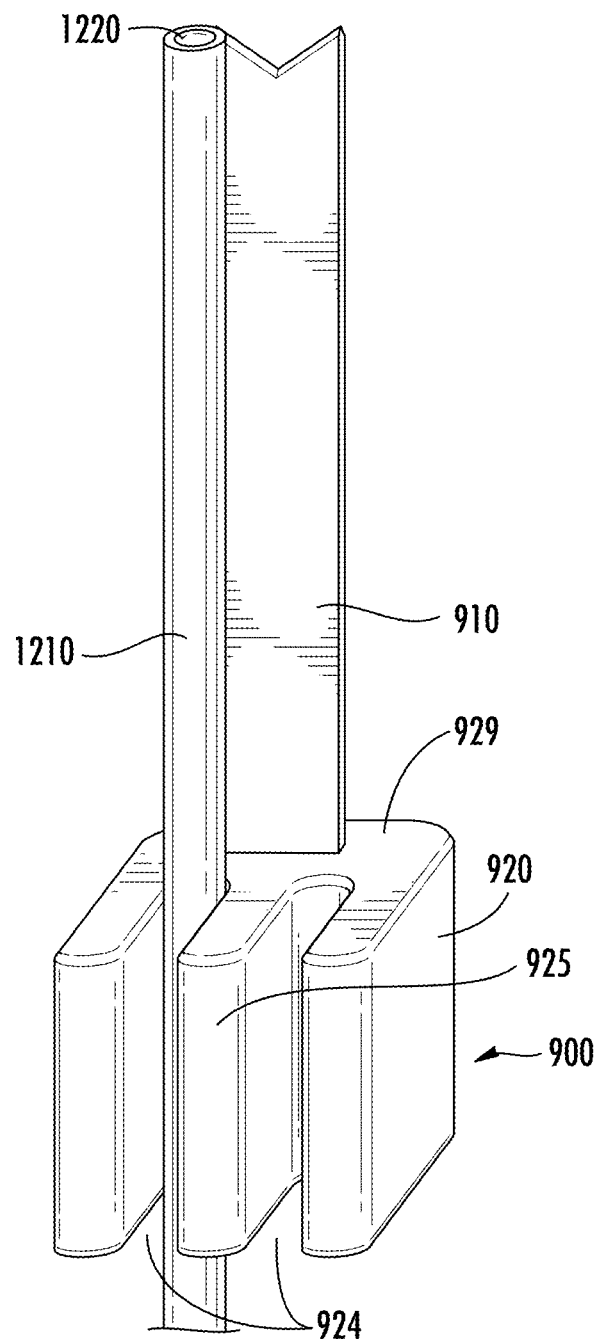

The handle 920 includes handle camera opening 924 separated by a slot divider 925. The handle camera openings 924 receive an endoscopic camera 1210 with an optical end 1220 that serves as the optics for a practitioner. The camera 1210 extends through the handle camera opening 924 into the guide camera opening 760, as shown in FIGS. 12A, 12B, and 13. The slot divider 925 guides and stabilizes the camera 1210. In use, the camera 1210, blade cutting tool 900, and guide 700 can all move independently of one another, which allows for better visibility (camera 1210), cutting accuracy (cutting tool 900) and tissue engagement (guide 700), as a practitioner moves each one during a surgery.

FIGS. 11, 12A, 1B, and 13 show the blade 910 entering the blade receiving slot 780, extending into the gap 730 and stopping when the blade cutting tool 900 bottom face 929 engages the guide 700 top face 725. FIG. 12A shows the blade 910 and camera 1210 in phantom within the guide 700.

Figure 11:
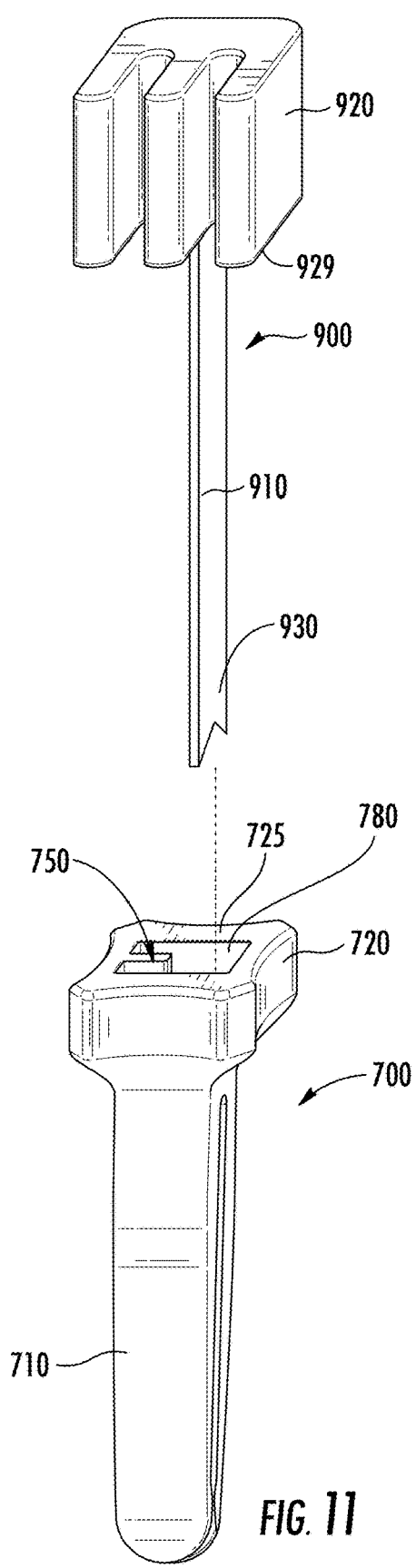
Figure 14:
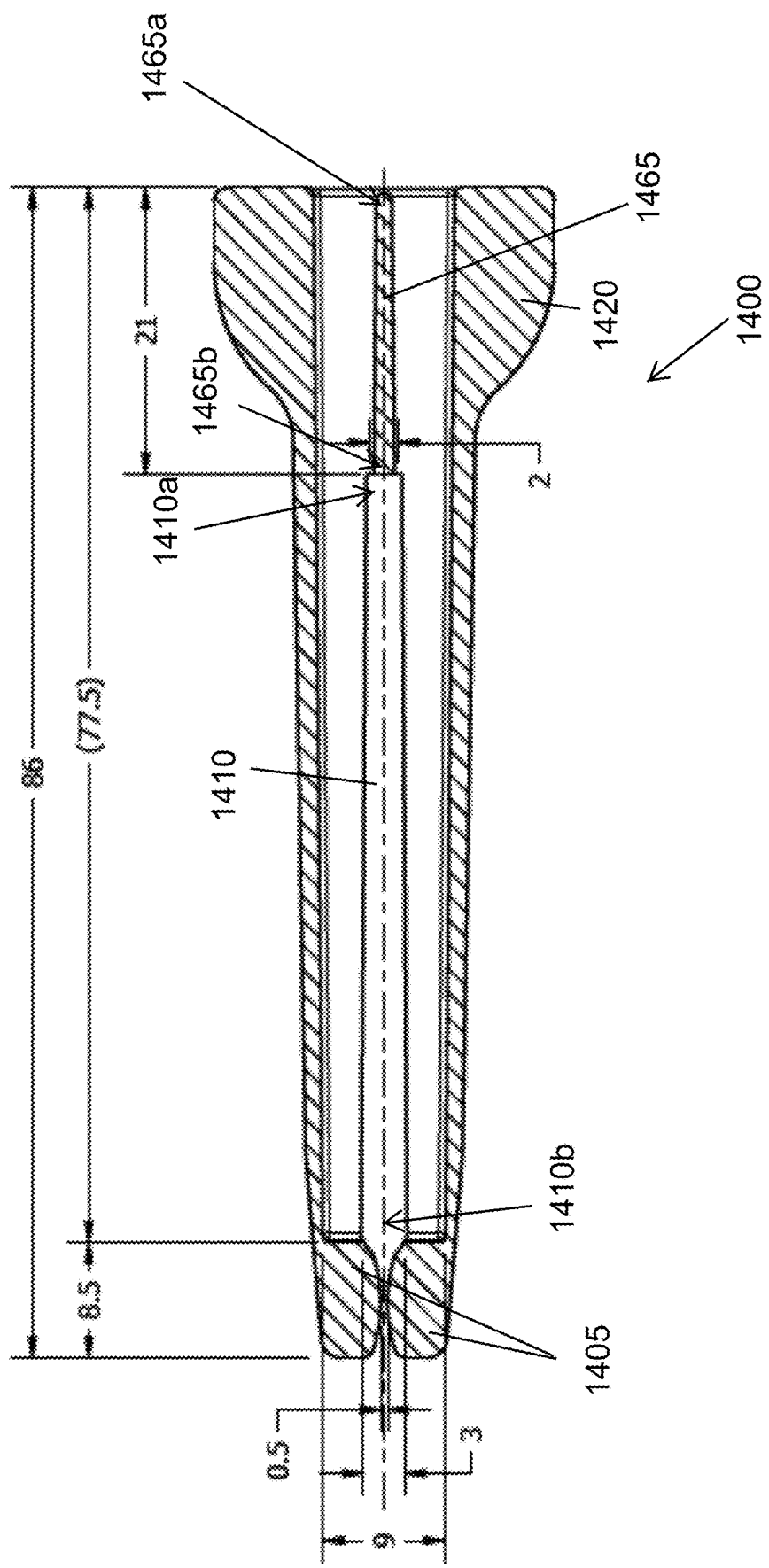
FIG. 14 is yet another embodiment showing a similar cross section to that shown in 8A-8A but with the device shown in FIGS. 11 and 12A.

FIG. 14 is yet another embodiment of a guide 1400 showing a similar cross section to that shown in 8A-8A but with a guide similar to that shown in FIGS. 11 and 12A configured to receive the blade. In this guide 1400, the gap 1410 narrows from the prongs 1405 towards the handle 1420 from a wider gap 1410b to a narrower gap 1410a. This narrowing gap follows the human geometry of the nerve, better gathering the nerve in the gap 1410 and preventing the tissue from bunching or folding in a uniform gap.

Similarly, the guide divider 1465 may also have a thickness that narrows from a divider thicker portion 1465b to a narrower portion 1465a to improve performance.

In FIG. 14, the dimensions shown in mm have been found to work well in practice in the surgeries mentioned above.

The device guide described herein may be shipped in sterile packaging to ensure sterility in use, which overcomes the issues with certain steel guides that must be sterilized on each use. Because it is plastic, the device may be discarded after use and easily replaced, thus making it less expensive than a stainless-steel tool but also safer. Similarly, the blade shown in in FIGS. 9-13 may be steel but in such a small quantity, may also be discarded.

In use, the device may encompass the transverse ligament therefore avoiding the challenge of synovium and fat dropping into view when cutting the ligament. This improves visibility because the surgeon isn't cutting underneath the ligament but encapsulating the ligament and cutting either antegrade or retrograde and seeing the ligament with a top view as well as bottom view while cutting.

Further, the top and bottom portions of the guide encompass the ligament and that makes the guide safer for ECTR.

As shown herein, the guide is as a unitary construction molded in plastic, although it is possible to 3D print the guide as well. Multi-piece construction is possible and may be advantageous in certain contexts.

The device is also made to accommodate both left and right hand for same procedure by just turning it upside down to always cut on the ulnar safe side of the hand, which is the ulnar side of anatomy.

Method Steps

Figure 15:
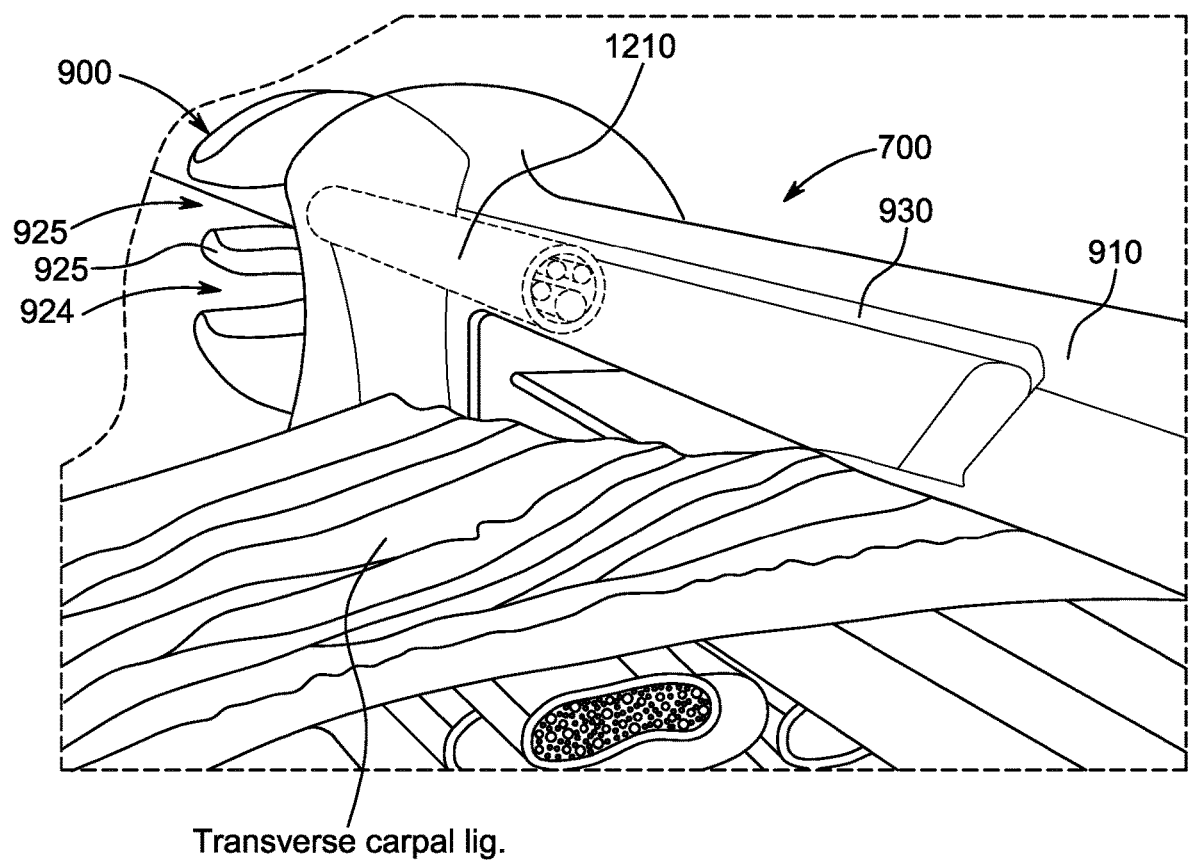
FIG. 15-17 show the device in use.
Figure 16:
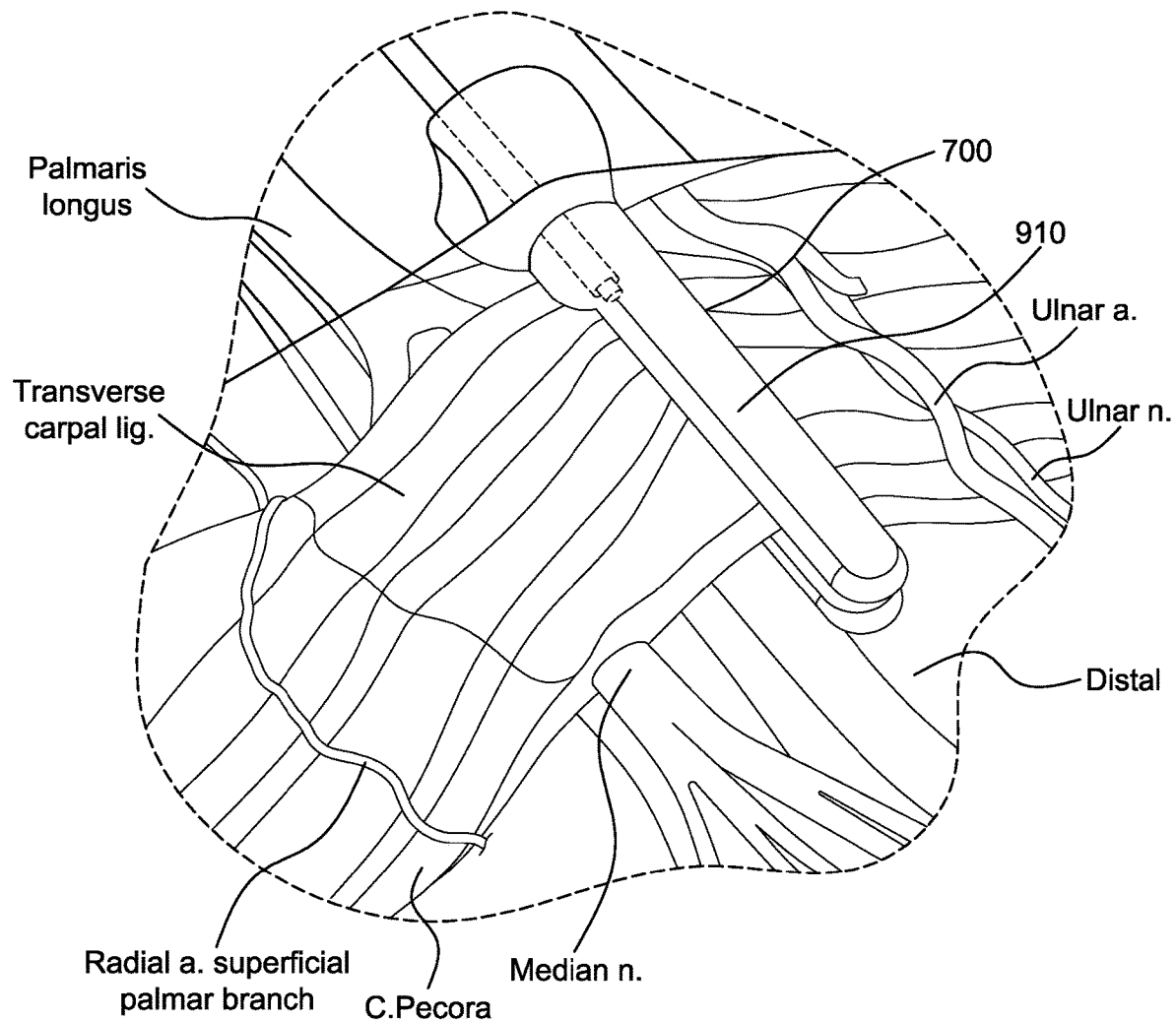
Figure 17:
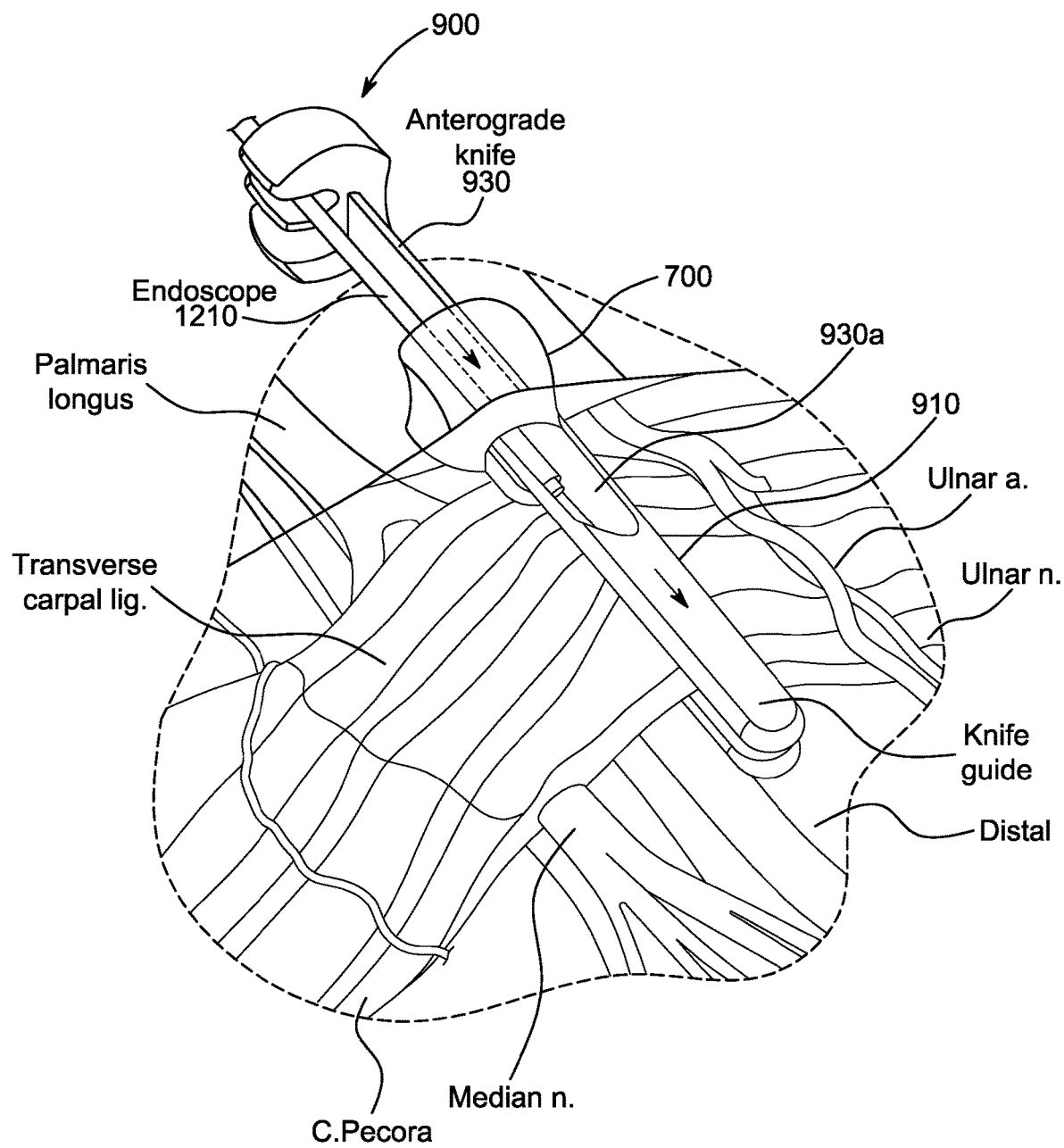

While the method of using the device has been previously described, it will be further explained with reference to FIGS. 15-17.

1. Incision. The surgeon makes a 1 cm transverse incision, 1 cm proximal to the distal wrist crease and ulnar to the palmaris longus. They then incise and resect the superficial forearm fascia proximal for 2 cm.

2. Dilation. Upon dilation of the carpal tunnel, the surgeon palpates the palm to feel the distal point of dilator and make mental mark. In general, this mark will be in line with the 3rd web space.

This mark will be the visual for dilating a pathway when the surgeon dilates above the transverse carpal ligament for the subcutaneous channel. It is important to create a subcutaneous channel that is parallel to the carpal tunnel to prevent divergence of the device's arms. This will allow for easy insertion of the device and for smooth gliding of the anterograde knife within the clip.

3. Placement of Device. The surgeon removes the dilator and places the guide 700 with one sleeve in the carpal tunnel and the other in the subcutaneous channel just created. The surgeon places the guide such that the appropriate letter is upright on the device (i.e. the "R" is facing up for a right carpal tunnel release or L for left, these markings being on the side of the head 720, with each letter having an upside-down orientation to the other). The blade slot 780 should be ulnar to the two scope portals.

With the device in place, the surgeon inserts a 4 mm or smaller scope 1210 in one of the two scope portals 760 that are radial to the blade slot 780. The two scope portals 760 allow visualization of the ligament both superficial and subsynovial.

4. Defining. The surgeon uses an included probe (not shown) to define the transverse carpal ligament and remove any synovium. The surgeon may use the probe to define the distal edge. If the surgeon cannot identify the distal edge from within carpal tunnel, then they can slide the guide distally until they can grasp the distal edge of ligament with the probe. After the surgeon has confirmed a clear channel superficial and deep to the transverse carpal ligament and have defined the distal edge, the ligament is ready to be transected.

5. Transection. The surgeon places the anterograde knife (with V-shaped leading blade edge 930a) 930 over the scope 1210 such that the knife blade 930 is aligned with the knife slot 780 on the device guide. The surgeon then proceeds to slide the knife 930 distally until transection is complete.

(Note: the device guide will stop the knife from sliding past the guide's end. The surgeon ensures that the guide is distal enough to transact the distal edge.)

Only a single pass is required with the anterograde knife.

Once transection is complete, the surgeon removes the blade 900 and guide 700. The surgeon then irrigates and closes the small incision, placing a light bandage over the closed incision.

While the invention has been described with reference to the embodiments above, a person of ordinary skill in the art would understand that various changes or modifications may be made thereto without departing from the scope of the claims.

The invention claimed is:

1. A method of using a surgical guide to transect a transverse carpal ligament comprising:
   providing the surgical guide and a surgical cutting tool comprising:
      the surgical guide comprising:
         a head comprising a tool opening therethrough; and
         two prongs attached to the head;
         wherein a gap separating the two prongs is in fluid communication with the tool opening in the head, wherein the gap narrows from the two prongs towards the head;
         wherein the tool opening in the head comprises a blade slot and at least one camera opening; and
      the surgical cutting tool comprising:
         a blade portion including a cutting blade; and
         a handle portion attached to the blade portion;
         wherein the blade portion is shaped to fit within the blade slot and extend into the gap between the two prongs;
         wherein the handle portion has a bottom face that contacts a guide end face to prevent the blade portion from extending further into the gap;
   providing an endoscopic camera that extends through a camera opening in the portion handle through the at least one camera opening of the surgical guide and into the gap;
   making a 1 cm transverse incision, 1 cm proximal to a distal wrist crease and ulnar to a palmaris longus;
   incising and resecting a superficial forearm fascia proximal for 2 cm;
   dilating a carpal tunnel using a dilator;
   palpating the palm to feel a distal point of the dilator;
   removing the dilator and placing the surgical guide with one prong of the two prongs on either side of a transverse carpal ligament;
   inserting a scope into one of the at least one camera opening;
   defining the transverse carpal ligament and removing any synovium;
   placing the surgical cutting tool through the blade slot;
   sliding the surgical cutting tool to transect the transverse carpal ligament; and
   removing the surgical cutting tool, scope, and the surgical guide from the transverse incision.

2. The method of claim 1, wherein the camera opening in the handle portion and the at least one camera opening of the surgical guide are in fluid communication with each other.

3. The method of claim 1, wherein the two prongs each include teeth extending into the gap.

4. The method of claim 1, wherein the head includes finger cutouts to assist in holding the surgical guide.

5. The method of claim 1, wherein at least one of the two prongs have a terminal end that is narrower than a prong end near the head.

6. The method of claim 1, wherein the tool opening is a single opening that includes the blade slot and the at least one camera opening of the surgical guide.

7. The method of claim 1, wherein the tool opening comprises two openings separated by a divider.

8. The method of claim 1, wherein the surgical guide is made from ABS plastic.

9. The method of claim 1, wherein the tool opening comprises a second camera opening.

10. The method of claim 1, wherein the at least one camera opening and the second camera opening are separated by a divider.

11. A method of using a surgical guide to transect a transverse carpal ligament comprising:
providing the surgical guide and a surgical cutting tool comprising:
the surgical guide comprising:
a head comprising a tool opening therethrough; and
two prongs attached to the head;
wherein a gap separating the two prongs is in fluid communication with the tool opening in the head,
wherein the gap narrows from the two prongs towards the head;
wherein the tool opening in the head comprises a blade slot and at least one camera opening; and
the surgical cutting tool comprising:
a blade portion including a cutting blade; and
a handle portion attached to the blade portion;
wherein the blade portion is shaped to fit within the blade slot and extend into the gap between the two prongs;
wherein the handle portion has a bottom face that contacts a guide end face to prevent the blade portion from extending further into the gap;
making a 1 cm transverse incision, 1 cm proximal to a distal wrist crease and ulnar to a palmaris longus;
incising and resecting a superficial forearm fascia proximal for 2 cm;
dilating a carpal tunnel using a dilator;
palpating the palm to feel a distal point of the dilator;
removing the dilator and placing the surgical guide with one prong of the two prongs on either side of a transverse carpal ligament;
inserting a scope into one of the at least one camera opening;
defining the transverse carpal ligament and removing any synovium;
placing the surgical cutting tool through the blade slot;
sliding the surgical cutting tool to transect the transverse carpal ligament; and
removing the surgical cutting tool, scope, and the surgical guide from the transverse incision;
wherein a camera opening in the surgical cutting tool and the at least one camera opening of the surgical guide are in fluid communication with each other.

12. The method of claim 11, further comprising the step of providing an endoscopic camera that extends through a camera opening in the surgical cutting tool through the at least one camera opening of the surgical guide and into the gap.

13. The method of claim 11, wherein the two prongs each include teeth extending into the gap.

14. The method of claim 11, wherein the head includes finger cutouts to assist in holding the surgical guide.

15. The method of claim 11, wherein at least one of the two prongs have a terminal end that is narrower than a prong end near the head.

16. The method of claim 11, wherein the tool opening is a single opening that includes the blade slot and the at least one of the surgical guide camera opening.

17. The method of claim 11, wherein the tool opening comprises two openings separated by a divider.

18. The method of claim 11, wherein the surgical guide is made from ABS plastic.

19. The method of claim 11, wherein the tool opening comprises a second camera opening.

20. The method of claim 11, wherein the at least one camera opening and the second camera opening are separated by a divider.

* * * * *